United States Patent [19]

Kabanov et al.

[11] Patent Number: 5,656,611
[45] Date of Patent: Aug. 12, 1997

[54] POLYNUCLEOTIDE COMPOSITIONS

[75] Inventors: Alexander Victorovich Kabanov, Omaha, Nebr.; Valery Yulievich Alakhov, D'Urfe, Canada; Sergey V. Vinogradov, Moscow, Russian Federation

[73] Assignee: Supratek Pharma Inc., Montreal, Canada

[21] Appl. No.: 342,209

[22] Filed: Nov. 18, 1994

[51] Int. Cl.⁶ .......................... A61K 48/00; A61K 9/127; C08F 2/00
[52] U.S. Cl. .......................... 514/44; 424/423; 424/450; 424/78.22; 424/78.36; 536/24.5; 514/772.1; 526/72
[58] Field of Search .......................... 536/24.5; 514/44, 514/668; 424/450, 423

[56] References Cited

U.S. PATENT DOCUMENTS

| | | | |
|---|---|---|---|
| 4,801,452 | 1/1989 | Hunter et al. | 424/94.63 |
| 4,873,083 | 10/1989 | Hunter et al. | 424/83 |
| 4,879,109 | 11/1989 | Hunter | 424/83 |
| 5,017,370 | 5/1991 | Hunter et al. | 424/83 |
| 5,030,448 | 7/1991 | Hunter | 424/83 |
| 5,041,288 | 8/1991 | Hunter | 424/83 |
| 5,047,236 | 9/1991 | Hunter et al. | 424/83 |

OTHER PUBLICATIONS

Mortensen and Pedersen, *Macromolecules* (1993), 26:805–812.
Linse, *Macromolecules* (1993), 26:4437–4449.
Mortensen and Brown, *Macromolecules* (1993), 26:4128–4135.
Schillen et al., *Macromolecules* (1994), 27:4825–4832.
Schillen et al., *Macromolecules* (1993), 26:3611–3614.
Linse, *Macromolecules* (1994), 27:2685–2693.
Zhou and Chu, *Macromolecules* (1994), 27:2025–2033.
Zhou and Chu, *Journal of Colloid and Interface Science* (1988), 126:171–180.
Zhou and Chu, *Macromolecules* (1988), 21:2548–2554.
Alexandridis, *Macromolecules* (1994), 27:2414–2425.
Alexandridis, *Langmuir* (1994), 10:2604–2612.
Hecht and Hoffman, *Langmuir* (1994), 10:86–91.
Schmolka, *Journal of the Am. Oil Chemists' Society* (1977), 54:110–116.
Wilhelm et al., *Macromolecules* (1991), 24:1033–1040.
Hoes et al., *J. Controlled Release* (1995), 2:205–213.
Duncan et al., *J. Controlled Release* (1989), 10:51–63.
Pratesi et al., *Br. J. Cancer* (1985), 52:841–848.
Page and Alakhov, *Proc Ann Meet Am. Assoc Cancer Res* (1992), 33:A3302.
Summary of article in *Nikkei Weekly*, Feb. 1994.
Slepnev et al., *Biochemistry International*, (1992) 26:587–595.
Kabanov et al., *Biochemistry International*, (May, 1992) 26:1035–1042.
Kabanov et al., *FEBS Letters*, (Dec. 1989) 258:343–345.
Kabanov et al., *J. Controlled Release*, (1992) 22:141–158.
Chekhonin et al., *FEBS*, (1991) 287:149–152.
"Highlights of U.S. Patents," *Anti–Viral Agents Bulletin*, Dec. 1993.
Kabanov et al., *Sov. Sci. Rev. D. Physiochem. Biol.* (1992), 11:1–75.
Kabanov et al., "Increasing the Transforming Activity of Plasmid DNA....," Plenum Publishing Corporation (1989), pp. 133–136.
Levashov et al., "Chemical Modification of Proteins (Enzymes) with Water Insoluble Reagents" (1984), pp. 295–297.
Levashov et al., "Translocation of Waterproofed Proteins (Enzymes) into Lysosymes" (1985).
Kabanov et al, *Collect. Czech. Chem. Commun.* (1989), 54:835–837.
Kabanov et al., *FEBS Letters* (1989), 250:238–240.
Kabanov et al., *Biol. Memb.* (1989), 2:1769–1785.
Kabanov et al., *Protein Engineering* (1989), 3:39–42.
Martinek et al., *Biochemica et Biophysica Acta* (1989), 981:161–172.
Kabanov et al., *Biomedical Science* (1990), 1:33–36.
Alakhov et al., *Biotechnology & Applied Biochemistry* (1990), 12:94–98.
Severin et al., *Advances in Enzyme Regulation* (1990), pp. 417–430.
Kabanov et al., *Biomedical Science* (1990), 1:63–68.
Melik–Nubarov et al., "Immunotherapeutic Prospects of Infectious Diseases," Masihi and Lange., Eds., Springer–Verleg, Berlin (1990), pp. 385–388.
Kabanov et al., *Collect. Czech. Chem. Commun.* (1990), 55:587–589.
Kabanov et al., *International Symposium on Virology, Immunology and Society*, Kozminov and Radavsky, Eds., UNESCO, Venice (1991), pp. 303–322.
Slepnev et al., *Bioconjugate Chem.* (1992), 3:273–274.
Kabanov, *International Conference on Pharmaceutical Ingredients and Intermediates*, Published by Manufacturing Chemists (1992), pp. 89–96.

(List continued on next page.)

Primary Examiner—Jacqueline M. Stone
Assistant Examiner—Patrick Twomey
Attorney, Agent, or Firm—Mathews, Collins, Shepherd & Gould, P.A.

[57] ABSTRACT

The invention provides compositions for stabilizing polynucleic acids and increasing the ability of polynucleic acids to cross cell membranes and act in the interior of a cell. In one aspect, the invention provides a polynucleotide complex between a polynucleotide and certain polyether block copolymers. Preferably the polynucleotide complex will further include a polycationic polymer. In another aspect, the invention provides a polynucleotide complex between a polynucleotide and a block copolymer comprising a polyether block and a polycation block. In yet another aspect, the invention provides polynucleotides that have been covalently modified at their 5' or 3' end to attach a polyether polymer segment. In still another aspect, the invention provides certain preferred polycationic polymers.

12 Claims, No Drawings

OTHER PUBLICATIONS

Melik–Nubarov et al., *Biochem. Molec. Biol. Int'l.* (1993), 29:939–947.

Kabanov et al., *Bioconjugate Chemistry* (1993), 4:448–454.

Sukhishvili et al., *Polymer Science* (1993), 35:1602–1606.

Kabanov and Alakhov, *Sixth International Symposium on Recent Advances in Drug Delivery Systems* (1993), pp. 73–76.

Kabanov and Alakhov, *J. Controlled Release* (1994), 28:15–35.

Kabanov et al., *FEBS Letters* (1990), 259:327–330.

Kabanov et al., *Biopolymers* (1994), 34:1437–1443.

Kabanov et al., *Polymer Preprints* (1991), 32:592–593.

Jones et al., *Biconjugate Chem.* (1994), 5:390–399.

Wei, et al., *Bioconjugate Chem.* (1994), 5:464–478.

Jäsche et al., *Nucleic Acids Research* (1994), 22:4810–4817.

A. V. Kabanov and V. P. Chekhonin, Polymeric Surfactant Micelles as Microcontainers for Neuroleptic targeting in the Brain, *J. Neuroimmunol.* (Suppl 1): 130 (1991).

A. V. Kabanov and V. Yu. Alakhov, *J. Controlled Release*, 28 (1994) 15–35.

Vinogradov et al., *Biochemical and Biophysical Research Communications*, vol. 203, No. 2 (Sep. 15, 1994) 959–966.

POLYNUCLEOTIDE COMPOSITIONS

The present invention relates to compositions of poly (nucleic acid) polymers such as RNA or DNA polymers and polycations that are associated, either covalently or noncovalently, with block copolymers of alkylethers. In a preferred embodiment, the poly(nucleic acids) will be complexed with a polycation. The nucleic acid is stabilized by the complex and, in the complex, has increased permeability across cell membranes. Accordingly, the complexes are well suited for use as vehicles for delivering nucleic acid into cells.

The use of "antisense" poly(nucleic acid) to treat genetic diseases, cell mutations (including cancer causing or enhancing mutations) and viral infections has gained widespread attention. This treatment tool is believed to operate, in one aspect, by binding to "sense" strands of mRNA encoding a protein believed to be involved in causing the disease state sought to be treated, thereby stopping or inhibiting the translation of the mRNA into the unwanted protein. In another aspect, genomic DNA is targeted for binding by the antisense polynucleotide (forming a triple helix), for instance, to inhibit transcription. See, Helene, *Anti-Cancer Drug Design*, 6:569 (1991). Once the sequence of the mRNA sought to be bound is known, an antisense molecule can be designed that binds the sense strand by the Watson-Crick base-pairing rules, forming a duplex structure analogous to the DNA double helix. *Gene Regulation: Biology of Antisense RNA and DNA*, Erikson and Ixzant, eds., Raven Press, New York, 1991; Helene, *Anti-Cancer Drug Design*, 6:569 (1991); Crooke, *Anti-Cancer Drug Design*, 6:609 (1991). A serious barrier to fully exploiting this technology is the problem of efficiently introducing into cells a sufficient number of antisense molecules to effectively interfere with the translation of the targeted mRNA or the function of DNA.

One method that has been employed to overcome this problem is to covalently modify the 5' or the 3' end of the antisense polynucleic acid molecule with hydrophobic substituents. These modified nucleic acids generally gain access to the cells interior with greater efficiency. See, for example, Kabanov et al., *FEBS Lett.*, 259:327 (1990); Boutorin et al., *FEBS Lett.*, 23:1382–1390, 1989; Shea et al, *Nucleic Acids Res.*, 18:3777–3783, 1990. Additionally, the phosphate backbone of the antisense molecules has been modified to remove the negative charge (see, for example, Agris et al., *Biochemistry*, 25:6268 (1986); Cazenave and Helene in *Antisense Nucleic Acids and Proteins: Fundamentals and Applications*, Mol and Van der Krol, eds., p. 47 et seq., Marcel Dekker, New York, 1991) or the purine or pyrimidine bases have been modified (see, for example, *Antisense Nucleic Acids and Proteins: Fundamentals and Applications*, Mol and Van der Krol, eds., p. 47 et seq., Marcel Dekker, New York, 1991; Milligan et al. in *Gene Therapy For Neoplastic Diseases*, Huber and Laso, eds., p. 228 et seq., New York Academy of Sciences, New York, 1994). Other attempts to overcome the cell penetration barrier include incorporating the antisense poly(nucleic acid) sequence into an expression vector that can be inserted into the cell in low copy number, but which, when in the cell, can direct the cellular machinery to synthesize more substantial amounts of antisense polynucleic molecules. See, for example, Farhood et al., *Ann. N.Y. Acad. Sci.*, 716:23 (1994). This strategy includes the use of recombinant viruses that have an expression site into which the antisense sequence has been incorporated. See, e.g., Boris-Lawrie and Temin, *Ann. N.Y. Acad. Sci*, 716:59 (1994). Others have tried to increase membrane permeability by neutralizing the negative charges on antisense molecules or other nucleic acid molecules with polycations. See, e.g. Kabanov et al., *Soviet Scientific Reviews*, Vol. 11, Part 2, 1992; Kabanov et al., *Bioconjugate Chemistry* 4:448 (1993); Wu and Wu, *Biochemistry*, 27:887–892, 1988; Behr et al., *Proc. Natl. Acad Sci U.S.A.* 86:6982–6986, 1989.

Of course, antisense polynucleic acid molecules are not the only type of polynucleic acid molecules that can usefully be made more permeable to cellular membranes. To make recombinant protein expression systems, the expression-directing nucleic acid must be transported across the membrane and into the eukaryotic or prokaryotic cell that will produce the desired protein. For gene therapy, medical workers try to incorporate, into one or more cell types of an organism, a DNA vector capable of directing the synthesis of a protein missing from the cell or useful to the cell or organism when expressed in greater amounts. The methods for introducing DNA to cause a cell to produce a new protein, ribozyme or a greater amount of a protein or ribozyme are called "transfection" methods. See, generally, *Neoplastic Diseases*, Huber and Lazo, eds., New York Academy of Science, New York, 1994; Feigner, *Adv. Drug Deliv. Rev.*, 5:163 (1990); McLachlin, et al., *Progr. Nucl. Acids Res. Mol. Biol.*, 38:91 (1990); Karlsson, S. Blood, 78:2481 (1991); Einerhand and Valerio, *Curr. Top. Microbiol Immunol.*, 177:217–235 (1992); Makdisi et al., *Prog. Liver Dis.*, 10:1 (1992); Litzinger and Huang, *Biochim. Biophys. Acta*, 1113:201 (1992); Morsy et al., *J.A.M.A.*, 270:2338 (1993); Dorudi et al., *British J. Surgery*, 80:566 (1993).

A number of the above-discussed methods of enhancing cell penetration by antisense nucleic acid are generally applicable methods of incorporating a variety of poly (nucleic acids) into cells. Other general methods include calcium phosphate precipitation of nucleic acid and incubation with the target cells (Graham and Van der Eb, *Virology*, 52:456, 1983), co-incubation of nucleic acid, DEAE-dextran and cells (Sompayrac and Danna, *Proc. Natl. Acad. Sci.*, 12:7575, 1981), electroporation of cells in the presence of nucleic acid (Potter et al., *Proc. Natl. Acad. Sci.*, 81:7161–7165, 1984), incorporating nucleic acid into virus coats to create transfection vehicles (Gitman et al., *Proc. Natl. Acad. Sci U.S.A.*, 82:7309–7313, 1985) and incubating cells with nucleic acid incorporated into liposomes (Wang and Huang, *Proc. Natl. Acad. Sci.*, 84:7851–7855, 1987).

Another problem in delivering nucleic acid to a cell is the extreme sensitivity of nucleic acids, particularly ribonucleic acids, to nuclease activity. This problem has been particularly germane to efforts to use ribonucleic acids as anti-sense oligonucleotides. Accordingly, methods of protecting nucleic acid from nuclease activity are desirable.

The invention is described below with reference to the fragmental constants developed by Hansch and Leo. See Hansch and Leo, *Substituent Constants for Correlation Analysis in Chemistry and Biology*, Wiley, New York, 1979; James, *Solubility and Related Properties*, Marcel Dekker, New York, 1986, pp. 320–325. These constants were developed for use in estimating the contribution of a portion of a molecule to the tendency of the molecule to partition between the phases formed by octanol-water mixtures. These constants are generally referred to as Hansch-Leo fragmental partition constants (hereinafter "Hansch-Leo fragmental constants").

The invention, in a first embodiment, relates to a polynucleotide composition comprising:

(a) a polynucleotide or derivative; and (b) a polyether block copolymer comprising an A-type segment and a B-type segment, wherein the A-type segment comprises a linear polymeric segment of relatively hydrophilic character, the repeating units of which contribute an average Hansch-Leo fragmental constant of about −0.4 or less and have molecular weight contributions between about 30 and about 500, wherein the B-type segment comprises a linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage. In a preferred first embodiment, the polyether block copolymer is selected from the group consisting of polymers of formulas

| | |
|---|---|
| A—B—A', | (I) |
| A—B, | (II) |
| B—A—B', | (III) |
| or | |
| L(R$^1$)(R$^2$)(R$^3$)(R$^4$) | (IV) | wherein A and A' are A-type linear polymeric segments, B and B' are B-type linear polymeric segments, and R$^1$, R$^2$, R$^3$ and R$^4$ are either block copolymers of formulas (I), (II) or (III) or hydrogen and L is a linking group, with the proviso that no more than two of R$^1$, R$^2$, R$^3$ or R$^4$ shall be hydrogen. In another preferred first embodiment of the invention, the polynucleotide composition shall further comprise a polycationic polymer comprising a plurality of cationic repeating units.

The composition provides an efficient vehicle for introducing polynucleotide into a cell. Accordingly, the invention also relates to a method of inserting poly(nucleic acid) into cells utilizing the first embodiment polynucleotide composition of the invention.

In a second embodiment, the invention provides a polynucleotide composition comprising:

(a) a polynucleotide or derivative;

(b) a block copolymer having a polyether segment and a polycation segment, wherein the polyether segment comprises at least an A-type block, and the polycation segment comprises a plurality of cationic repeating units. In a preferred second embodiment, the copolymer comprises a polymer of formula:

| | |
|---|---|
| B—A—R, | (V-a) |
| A—R, | (VI-a) |
| A—R—A', | (VII) |
| and | |
| R—A—R', | (VIII-a) |
| A—B—R, | (V-b) |
| A—R—B, | (VI-b) |
| R—A—B | (VIII-b) | wherein the A, A' and B are as described above, wherein R and R' are polymeric segments comprising a plurality of cationic repeating units, wherein each cationic repeating unit in a segment may be the same or different from another unit in the segment. The polymers of this embodiment can be termed "polyether/polycation" polymers. The R and R', blocks can be termed "R-type" polymeric segments or blocks.

The polynucleotide composition of the second embodiment provides an efficient vehicle for introducing the polynucleotide into a cell. Accordingly, the invention also relates to a method of inserting poly(nucleic acid) into cells utilizing the second embodiment composition of the invention.

In a third embodiment, the invention provides a polynucleotide composition comprising a polynucleotide derivative comprising a polynucleotide segment and a polyether segment attached to one or both of the polynucleotide 5' and 3' ends, wherein the polyether comprises an A-type polyether segment. In a preferred third embodiment, the derivative comprises a block copolymer of formulas:

| | |
|---|---|
| A-pN, | (IX-a) |
| pN—A, | (X-a) |
| A-pN—A', | (XI) |
| pN—A—B, | (XII) |
| B—A-pN | (XIII) |
| A-pN—R, | (IX-b) |
| R—A-pN, | (IX-c) |
| A—R-pN, | (IX-d) |
| pN—A—R, | (X-b) |
| R-pN—A, | (X-c) |
| pN—R—A | (X-c) | wherein pN represents a polynucleotide having 5' to 3' orientation, and A, A' and B are polyether segments as described above. In another preferred third embodiment, the polynucleotide complex comprises a polycationic polymer.

Polymers of formulas (I), (II), (III) or (IV) can also be mixed with each other or can be mixed either additionally or alternatively with one or more of the polymers of formula (V-a or b), (VI-a or b), (VII-a or b) and (VIII-a or b) and/or with polynucleotide derivatives of formulas (IX-a,b,c or d), (X-a,b,c or d), (XI), (XII) or (XIII) to provide an efficient vehicle for delivering poly(nucleic acid) to the interior of cells.

The polynucleotide composition of the third embodiment provides an efficient vehicle for introducing the polynucleotide into a cell. Accordingly, the invention also relates to a method of inserting poly(nucleic acid) into cells utilizing the third embodiment composition of the invention.

A fourth embodiment of the invention relates to a polyether-polycation copolymer comprising a polymer, a polyether segment and a polycationic segment comprising a plurality of cationic repeating units of formula —NH—R$^0$, wherein R$^0$ is a straight chain aliphatic group of 2 to 6 carbon atoms, which may be substituted, wherein said polyether segments comprise at least one of an A-type of B-type segment. In a preferred fourth embodiment, the polycation polymer comprises a polymer according to formulas:

$$B-A-R, \quad (V)$$

$$A-R, \quad (VI)$$

$$A-R-A', \quad (VII)$$

and $$R-A-R', \quad (VIII)$$

wherein A, A' and B are as described above, wherein R and R' are polymeric segments comprising a plurality of cationic repeating units of formula —NH—R°—, wherein R° is a straight chain aliphatic group having from 2 to 6 carbon atoms, which may be substituted. Each —NH—R°— repeating unit in an R-type segment can be the same or different from another —NH—R°— repeating unit in the segment. A preferred fourth embodiment further comprises a polynucleotide or derivative.

In a fifth embodiment, the invention provides a polycationic polymer comprising a plurality of repeating units of formula:

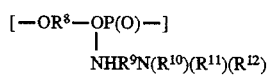

where $R^8$ is:

(1) —$(CH_2)_n$—$CH(R^{13})$—, wherein n is an integer from 0 to about 5 and $R^{13}$ is hydrogen, cycloalkyl having 3–8 carbon atoms, alkyl having 1–6 carbon atoms, or $(CH_2)_m R^{14}$, where m is an integer from 0 to about 12 and $R^{14}$ is a lipophilic substituent of 6 to 20 carbon atoms;

(2) a carbocyclic group having 3–8 ring carbon atoms, wherein the group can be for example, cycloalkyl or aromatic groups, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro or chloro substituents; or (3) a heterocyclic group, having 3–8 ring atoms, which can include heterocycloalkyl or heteroaromatic groups, which can include from 1 to 4 heteroatoms selected from the group consisting of oxygen, nitrogen, sulfur and mixtures thereto, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro or chloro substituents. $R^9$ is a straight chain aliphatic group of 1 to 12 carbon atoms, and $R^{10}$, $R^{11}$ and $R^{12}$ are independently hydrogen, an alkyl group of 1–4 carbon atoms. $R^9$ preferably comprises 2–10 carbon atoms, more preferably, 3–8. $R^{14}$ preferably includes an intercalating group, which is preferably an acrydine or ethydium bromide group. The number of such repeating units in the polymer is preferably between about 3 and 50, more preferably between about 5 and 20. This polymer structure can be incorporated into other embodiments of the invention as an R-type segment or polycationic polymer. The ends of this polymer can be modified with a lipid substituent. The monomers that are used to synthesize polymers of this embodiment are suitable for use as the monomers fed to a DNA synthesizer, as described below. Thus, the polymer can be synthesized very specifically. Further, the additional incorporation of polynucleotide sequences, polyether blocks, and lipophilic substituents can be done using the advanced automation developed for polynucleotide syntheses. The fifth embodiment also encompasses this method of synthesizing a polycationic polymer.

Filed concurrently with this application was an application entitled "POLYMER LINKED BIOLOGICAL AGENTS," Docket No. 313257-101, with Alexander Victorovich Kabanov and Valery Yulievich Alakhov as the named inventors. The entire disclosure of this concurrently filed application is incorporated herein by reference.

The degree of polymerization of the hydrophilic (A-type) blocks or the hydrophobic (B-type) blocks of formulas (I)–(XIII) can preferably be between about 5 and about 400. More preferably, the degree of polymerization shall be between about 5 and about 200, still more preferably, between about 5 and about 80. The degree of polymerization of the R-type polycation blocks can preferably be between about 2 and about 300. More preferably, the degree of polymerization shall be between about 5 and about 180, still more preferably, between about 5 and about 60. The degree of polymerization of the polycationic polymer can preferably be between about 10 and about 10,000. More preferably, the degree of polymerization shall be between about 10 and about 1,000, still more preferably, between about 10 and about 100.

The repeating units that comprise the blocks, for A-type, B-type and R-type blocks, will generally have molecular weight between about 30 and about 500, preferably between about 30 and about 100, still more preferably between about 30 and about 60. Generally, in each of the A-type or B-type blocks, at least about 80% of the linkages between repeating units will be ether linkages, preferably, at least about 90% will be ether linkages, more preferably, at least about 95% will be ether linkages. Ether linkages, for the purposes of this application, encompass glycosidic linkages (i.e., sugar linkages). However, in one aspect, simple ether linkages are preferred.

Preferably, all of the repeating units that comprise blocks A or A' have a Hansch-Leo fragmental constant of less than about −0.4, more preferably, less than about −0.5, still more preferably, less than about −0.7. Preferably, all of the repeating units that comprise blocks B or B' have a Hansch-Leo fragmental constant of about −0.30 or more, more preferably about −0.20 or more.

The polynucleotide component (pN) of formulas (IX) through (XIII) will preferably comprise from about 5 to about 1,000,000 bases, more preferably about 5 to about 100,000 bases, yet more preferably about 10 to about 10,000 bases.

The polycationic polymers and the R-type blocks have several positively ionizable groups and a net positive charge at physiologic pH. The polyether/polycation polymers of formulas (V)–(VIII) can also serve as polycationic polymers. Preferably, the polycationic polymers and R-type blocks will have at least about 3 positive charges at physiologic pH, more preferably, at least about 6, still more preferably, at least about 12. Also preferred, are polymers or blocks that, at physiologic pH, can present positive charges with about a spacing between the charges of about 3 Å to about 10 Å. The spacings established by aminopropylene repeating units, or by mixtures of aminopropylene and aminobutylene repeating units are most preferred. Accordingly, for instance, polycationic segments that utilize a ($NHCH_2CH_2CH_2$) repeating unit, or a mixture of ($NHCH_2CH_2CH_2$) and ($NHCH_2CH_2CH_2CH_2$) repeating units, are preferred.

Polyether/polycation polymers of formulas (V)–(VIII) comprising a —NH—R°— repeating unit are also preferred.

R⁰ is preferably an ethylene, propylene, butylene, or pentylene, which can be modified. In a preferred embodiment, in at least one of the repeating units, R⁰ includes a DNA intercalating group such as an ethidium bromide group. Such intercalating groups can increase the affinity of the polymer for nucleic acid. Preferred substitutions on R⁰ include alkyl of 1–6 carbons, hydroxy, hydroxyalkyl, wherein the alkyl has 1–6 carbon atoms, alkoxy having 1–6 carbon atoms, an alkyl carbonyl group having 2–7 carbon atoms, alkoxycarbonyl wherein the alkoxy has 1–6 carbon atoms, alkoxycarbonylalkyl wherein the alkoxy and alkyl each independently has 1–6 carbon atoms, alkylcarboxyalkyl wherein each alkyl group has 1–6 carbon atoms, aminoalkyl wherein the alkyl group has 1–6 carbon atoms, alkylamino or dialkylamino where each alkyl group independently has 1–6 carbon atoms, mono- or di-alkylaminoalkyl wherein each alkyl independently has 1–6 carbon atoms, chloro, chloroalkyl wherein the alkyl has from 1–6 carbon atoms, fluoro, fluoroalkyl wherein the alkyl has from 1–6 carbon atoms, cyano, or cyano alkyl wherein the alkyl has from 1–6 carbon atoms or a carboxyl group. More preferably, R⁰ is propylene or butylene.

Polymers according to the first embodiment of the invention are exemplified by the block copolymers having the formulas:

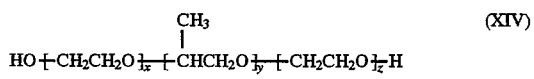

or,

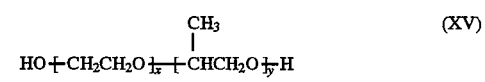

or,

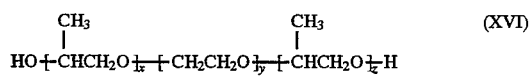

or,

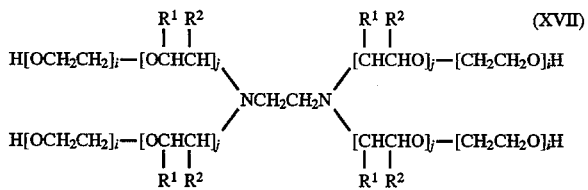

in which x, y, z, i and j have values from about 5 to about 400, preferably from about 5 to about 200, more preferably from about 5 to about 80, and wherein for each $R^1$, $R^2$ pair, one shall be hydrogen and the other shall be a methyl group. Formulas (XIV) through (XVI) are oversimplified in that, in practice, the orientation of the isopropylene radicals within the B block will be random. This random orientation is indicated in formula (XVII), which is more complete. Such poly(oxyethylene)-poly(oxypropylene) compounds have been described by Santon, Am. Perfumer Cosmet. 72(4) :54–58 (1958); Schmolka, Loc. cit. 82(7):25–30 (1967); Non-ionic Surfactants, Schick, ed. (Dekker, NY, 1967), pp. 300–371. A number of such compounds are commercially available under such generic trade names as "poloxamers," "pluronics" and "synperonics." Pluronic polymers within the B-A-B formula are often referred to as "reversed" pluronics, "pluronic R" or "meroxapol." The "polyoxamine" polymer of formula (XVII) is available from BASF (Wyandotte, Mich.) under the tradename Tetronic™. The order of the polyoxyethylene and polyoxypropylene blocks represented in formula (XVII) can be reversed, creating Tetronic R™, also available from BASF. See, Schmolka, J. Am. Oil Soc., 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename Pluradot™.

The diamine-linked pluronic of formula (XVII) can also be a member of the family of diamine-linked polyoxyethylene-polyoxypropylene polymers of formula:

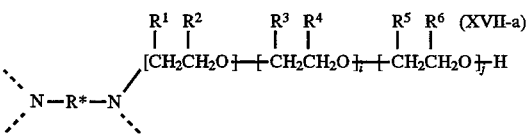

wherein the dashed lines represent symmetrical copies of the polyether extending off the second nitrogen, $R^*$ an alkylene of 2 to 6 carbons, a cycloalkylene of 5 to 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen.

Those of ordinary skill in the art will recognize, in light of the discussion herein, that even when the practice of the invention is confined for example, to poly(oxyethylene)-poly(oxypropylene) compounds, the above exemplary formulas are too confining. An important feature is that the average Hansch-Leo fragmental constant of the monomers in an A-type block be about–0.4 or less. Thus, the units making up the first block need not consist solely of ethylene oxide. Similarly, not all of the B-type block need consist solely of propylene oxide units. Instead, the blocks can incorporate monomers other than those defined in formulas (XIV)–(XVII), so long as the parameters of the first embodiment are maintained. Thus, in the simplest of examples, at least one of the monomers in block A might be substituted with a side chain group as previously described.

In another aspect, the invention relates to a polynucleotide complex comprising a block copolymer at least one of formulas (I)–(XIII), wherein the A-type and B-type blocks are substantially made up of repeating units of formula —O—$R^5$, where $R^5$ is:

(1) —$(CH_2)_n$—$CH(R^6)$—, wherein n is an integer from 0 to about 5 and $R^6$ is hydrogen, cycloalkyl having 3–8 carbon atoms, alkyl having 1–6 carbon atoms, phenyl, alkylphenyl wherein the alkyl has 1–6 carbon atoms, hydroxy, hydroxyalkyl, wherein the alkyl has 1–6 carbon atoms, alkoxy having 1–6 carbon atoms, an alkyl carbonyl group having 2–7 carbon atoms, alkoxycarbonyl, wherein the alkoxy has 1–6 carbon atoms, alkoxycarbonylalkyl, wherein the alkoxy and alkyl each independently has 1–6 carbon atoms, alkylcarboxyalkyl, wherein each alkyl group has 1–6 carbon atoms, aminoalkyl wherein the alkyl group has 1–6 carbon atoms, alkylamine or dialkylamino, wherein each alkyl independently has 1–6 carbon atoms, mono- or di-alkylaminoalkyl wherein each alkyl independently has 1–6 carbon atoms, chloro, chloroalkyl wherein the alkyl has from 1–6 carbon atoms, fluoro, fluoroalkyl wherein the alkyl has from 1–6 carbon atoms, cyano or cyano alkyl wherein the alkyl has from 1–6 carbon atoms or carboxyl;

(2) a carbocyclic group having 3–8 ring carbon atoms, wherein the group can be for example, cycloalkyl or aromatic groups, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfohyl, hydroxy, carboxy, fluoro or chloro substitutions, or (3) a heterocyclic group, having 3–8 ring atoms, which can include heterocycloalkyl or heteroaromatic groups, which can include from 1 to 4 heteroatoms selected from the group consisting of oxygen, nitrogen, sulfur and mixtures thereto, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfohyl, hydroxy, carboxy, fluoro or chloro substitutions.

Preferably, n is an integer from 1 to 3. The carbocyclic or heterocyclic groups comprising $R^5$ preferably have from 4–7 ring atoms, more preferably 5–6. Heterocycles preferably include from 1–2 heteroatoms, more preferably, the heterocycles have one heteroatom. Preferably, the heterocycle is a carbohydrate or carbohydrate analog. Those of ordinary skill will recognize that the monomers required to make these polymers are synthetically available. In some cases, polymerization of the monomers will require the use of suitable protective groups, as will be recognized by those of ordinary skill in the art. Generally, the A and B-type blocks are at least about 80% comprised of $-OR^5-$ repeating units, more preferably at least about 90%, yet more preferably at least about 95%.

In another aspect, the invention relates to a polynucleotide complex comprising a block copolymer of one of formulas (I)–(XIII) wherein the A-type and B-type blocks consist essentially of repeating units of formula $-O-R^7-$, wherein $R^7$ is a $C_1$ to $C_6$ alkyl group.

The Hansch-Leo estimate of the octanol-water partitioning coefficient (P) for an organic molecule is calculated by the following formula:

$$\text{Log } P = \Sigma a_n f_n + \Sigma b_m F_m$$

where the $f_n$ values are the fragmental constants for the different groups in the molecule, the $a_n$ values are the number of any type of group in the molecule, the $F_m$ values are factors for certain molecular features such as single bonds or double bonds, and the $b_m$ values are the number of any such molecular feature. For instance, the Hansch-Leo fragmental constant for an ethylene oxide repeating unit ($-CH_2CH_2O-$) would be:

$$2f_c + 4f_H + f_O + (4-1)F_b = 2(0.20) + 4(0.23) + (-1.82) + 3(-0.12) = -0.86$$

The Hansch-Leo fragmental constant for a propylene oxide ($-CH_2CHCH_3)O-$) repeating unit would be:

$$2f_c + f_{CH^3} + 3f_H + f_O + (4-1)F_b = 2(0.2) + 0.89 + 3(0.23) + (-1.28) + 3(-0.12) = -0.2$$

Those of ordinary skill in the art will recognize that the Hansch-Leo approach to estimating partition constants, in which approach the Hansch-Leo fragmental constants are applied, does not yield precisely the empirical partition constant. See Hansch and Leo, *Substituent Constants for Correlation Analysis in Chemistry and Biology*, Wiley, New York, 1979; James, *Solubility and Related Properties*, Marcel Dekker, New York, 1986, pp. 320–325. However, the approach is precise enough to define the hydrophobicity features of the polymeric delivery vehicle.

A wide variety of nucleic acid molecules can be the nucleic acid component of the composition. These include natural and synthetic DNA or RNA molecules and nucleic acid molecules that have been covalently modified (to incorporate groups including lipophilic groups, photo-induced crosslinking groups, alkylating groups, organometallic groups, intercalating groups, lipophilic groups, biotin, fluorescent and radioactive groups, and groups that modify the phosphate backbone). Such nucleic acid molecules can be, among other things, antisense nucleic acid molecules, gene-encoding DNA (usually including an appropriate promotor sequence), ribozymes oligonucleotide α-anomers, ethylphosphotriester analogs, alkylphosphomates, phosphorothionate and phosphorodithionate oligonucleotides, and the like. In fact, the nucleic acid component can be any nucleic acid that can beneficially be transported into a cell with greater efficiency, or stabilized from degradative processes, or improved in its biodistribution after administration to an animal.

Examples of useful polymers pursuant to formulas (V)–(VIII) include the poly(oxyethylene)-poly-L-lysine) diblock copolymer of the following formula:

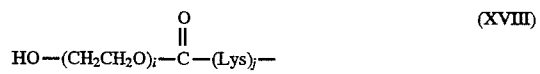

wherein i is an integer of from about 5 to about 100, and j is an integer from about 4 to about 100. A second example is the poly(oxyethylene)-poly-(L-alanine-L-lysine) diblock copolymer of formula:

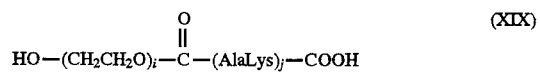

wherein i is an integer of from about 5 to about 100 and j is an integer from about 4 about 100. A third example is the poly(oxyethylene)-poly(propyleneimine/butyleneimine) diblock copolymer of the following formula:

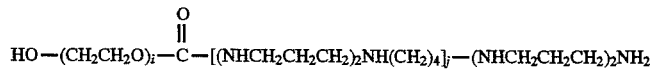

wherein i is an integer from about 5 about 200 and j is an integer from 1 to about 10. A fourth example is the poly(oxyethylene)-poly(N-ethyl-4-vinylpyridinium bromide) ("pOE-pEVP-Br") of formula:

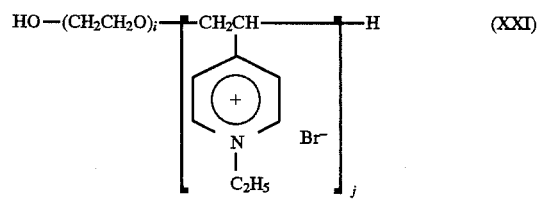

wherein i is an integer of from about 5 to about 100 and j is an integer of from about 10 to about 500. Still another example is the polymer of formula:

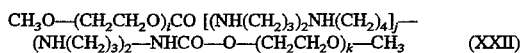
(XXII)

wherein i is an integer from about 10 to about 200, j is an integer from about 1 to about 8, and k is an integer from about 10 to about 200. Still another example is the polymer of formula:

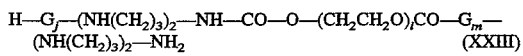
(XXIII)

wherein "G" comprises. —(NH(CH$_2$)$_3$)$_3$—CH$_2$—, i and j are as defined for formula (XVIII), and m is an integer from about 1 to about 8.

The block copolymers utilized in the invention, will typically, under certain circumstances, form micelles of from about 10 nm to about 100 nm in diameter. Micelles are supramolecular complexes of certain amphiphilic molecules that form in aqueous solutions due to microphase separation of the nonpolar portions of the amphiphiles. Micelles form when the concentration of the amphiphile reaches, for a given temperature, a critical micellar concentration ("CMC") that is characteristic of the amphiphile. Such micelles will generally include from about 10 to about 300 block copolymers. By varying the sizes of the hydrophilic and hydrophobic portions of the block copolymers, the tendency of the copolymers to form micelles at physiological conditions can be varied. The micelles have a dense core formed by the water insoluble repeating units of the B blocks and charge-neutralized nucleic acids, and a hydrophilic shell formed by the A blocks. The micelles have translational and rotational freedom in solution, and solutions containing the micelles have low viscosity similar to water. Micelles formation typically occurs at copolymer concentrations from about 0.001 to 5% (w/v). Generally, the concentration of polycationic polymers and polynucleic acid will be less than the concentration of copolymers in the polynucleotide compositions, preferably at least about 10-fold less, more preferably at least about 50-fold.

At high concentrations, some of the block copolymers utilized in the invention will form gels. These gels are viscous systems in which the translational and rotational freedom of the copolymer molecules is significantly constrained by a continuous network of interactions among copolymer molecules. In gels, microsegregation of the B block repeating units may or may not occur. To avoid the formation of gels, polymer concentrations (for both block copolymers and polyether/polycation polymers) will preferably be below about 15% (w/v), more preferably below about 10%, still more preferably below about 5%. In the first embodiment of the invention, it is more preferred that gels be avoided.

When the polynucleotide composition includes cationic components, the cations will associate with the phosphate groups of the polynucleotide, neutralizing the charge on the phosphate groups and rendering the polynucleotide component more hydrophobic. The neutralization is preferably supplied by cations on R-type polymeric segments or on polycationic polymers. However, the phosphate charge can also be neutralized by chemical modification or by association with a hydrophobic cations such as N-[1-(2,3-dioleyloxy)-N,N'-3-methylammonium chloride]. In aqueous solution, the charge neutralized polynucleotides are believed to participate in the formation of supramolecular, micelle-like particles that can be termed "polynucleotide complexes." The hydrophobic core or the complex comprises the charge-neutralized polynucleotides and the B-type copolymer blocks. The hydrophilic shell comprises the A-type copolymer blocks. The size of the complex will generally vary from about 10 nm to about 100 nm in diameter. In some contexts, it is practical to isolate the complex from unincorporated components. This can be done, for instance, by gel filtration chromatography.

The ratio of the components of the polynucleotide composition is an important factor in optimizing the effective transmembrane permeability of the polynucleotides in the composition. This ratio can be identified as ratio $\phi$, which is the ratio of positively charged groups to negatively charged groups in the composition at physiological pH. If $\phi<1$, the complex contains non-neutralized phosphate from the polynucleotide. The portions of the polynucleotides adjacent to the non-neutralized charges are believed to be a part of the shell of a polynucleotide complex. Correspondingly, if $\phi>1$, the polycationic polymer or R-type segment will have non-neutralized charges, and the un-neutralized portions will fold so that they form a part of the shell of the complex. Generally, $\phi$ will vary from about 0 (where there are no cationic groups) to about 100, preferably $\phi$ will range between about 0.01 and about 50, more preferably, between about 0.1 and about 20. $\phi$ can be varied to increase the efficiency of transmembrane transport and, when the composition comprises polynucleotide complexes, to increase the stability of the complex. Variations in $\phi$ can also affect the biodistribution of the complex after administration to an animal. The optimal $\phi$ will depend on, among other things, (1) the context in which the polynucleotide composition is being used, (2) the specific polymers and oligonucleotides being used, (3) the cells or tissues targeted, and (4) the mode of administration.

It will in some circumstances be desirable to incorporate, by noncovalent association, targeting molecules. See, for example, Kabanov et al., *J. Controlled Release*, 22:141 (1992). The targeting molecules that can be associated with the composition typically have a targeting group having affinity for a cellular site and a hydrophobic group. The targeting molecule will spontaneously associate with the polynucleotide complex and be "anchored" thereto through the hydrophobic group. These targeting adducts will typically comprise about 10% or less of the copolymers in a composition.

In the targeting molecule, the hydrophobic group can be, among other things, a lipid group such as a fatty acyl group. Alternately, it can be a block copolymer or another natural synthetic polymer. The targeting group of the targeting molecule will frequently comprise an antibody, typically with specificity for a certain cell surface antigen. It could also be, for instance, a hormone having a specific interaction with a cell surface receptor, or a drug having a cell surface receptor. For example, glycolipids could serve to target a polysaccharide receptor.

For polyethylene oxide-polypropylene oxide copolymer, the hydrophilic/hydrophobic properties, and micelle forming properties of a block copolymer are, to a certain degree, related to the value of the ratio, n. The ratio, n, is defined as:

$$n=(|B|/|A|)\times(b/a)=(|B|/|A|)\times 1.32$$

where |B| and |A| are the number of repeating units in the hydrophobic and hydrophilic blocks of the copolymer, respectively, and b and a are the molecular weights for the respective repeating units. The value of n will typically be between about 0.2 and about 9.0, more preferably, between about 0.2 and about 1.5. Where mixtures of block copolymers are used, n will be the weighted average of n for each contributing copolymers, with the averaging based on the weight portions of the component copolymers. When copolymers other than polyethylene oxide-polypropylene oxide copolymers are used, similar approaches can be developed to relate the hydrophobic/hydrophilic properties of one member of the class of polymers to the properties of another member of the class.

The polynucleotide compositions of the invention can be administered orally, topically, rectally, vaginally, by pulmonary route by use of an aerosol, or parenterally, i.e. intramuscularly, subcutaneously, intraperitoneally or intravenously. The polynucleotide compositions can be administered alone, or it can be combined with a pharmaceutically-acceptable carrier or excipient according to standard pharmaceutical practice. For the oral mode of administration, the polynucleotide compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the polynucleotide compositions can be combined with emulsifying and suspending agents. If desired, certain sweetening and/or flavoring agents can be added. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

EXAMPLE 1—TRANSFECTION EFFICIENCIES—FIRST EMBODIMENT COMPLEX

This experiment sought to introduce plasmid p$\beta$-Gal into NIH 3T3 cells, a mouse mamory tumor cell line. Plasmid p$\beta$-Gal comprises plasmid pUC19 (available from Institute of Gene Biology, Russian Academy of Sciences) into which a hybrid of a eukaryotic transcription unit and a E. coli $\beta$-galactosidase has been incorporated. With this plasmid, the efficiency of cell uptake can be measured by measuring $\beta$-galactosidase activity extractable from the treated cells. The copolymer utilized was a triblock copolymer of formula (XIV) wherein x plus z was 51 and y was 39 (hereinafter "Pluronic A"). The polycation utilized was poly(N-ethyl-4-vinylpyridinium bromide) ("pEVP-Br"). A 10 µg/ml solution of p$\beta$-Gal (predominantly supercoiled) was prepared in a solution of PBS containing 10 mg/ml of pluronic A and 45 µg/ml of pEVP-Br. These amounts were calculated to provide a ratio of polycation basic groups to plasmid phosphate groups of about 10. The ratio of pluronic A to DNA was about $10^4$. This stock preparation was filter sterilized and a portion was diluted ten fold with serum-free Dulbecco's Modified Eagle's Medium ("DMEM"), so that the concentration of p$\beta$-Gal was 1 µg/ml. This solution was the "Pluronic A transfecting medium."

The NIH 3T3 cells were grown in monolayer culture at 37° C. under 5% $CO_2$, utilizing a DMEM medium containing 2 mM glutamine and 10% fetal calf serum ("FCS"). Cells were grown in monolayer culture were scraped and prepared for the transaction process by washing three times with fresh medium.

Alloquots of washed cells that were to be transformed by the method of the invention were suspended at a concentration of $10^6$ cells/ml in Pluronic A transfecting medium. The suspended cells were incubated for 2 hours at 37° C. and under 5% $CO_2$. The cells were then washed with fresh medium and re-plated.

Alloquots of cells that were to be transfected by calcium phosphate precipitation were transfected as recommended by Promega of Madison, Wisconsin, in their manuscript *Profection Mammalian Transfection Systems*, Technical Manual, 1990. Specifically, p$\beta$-Gal was mixed with 0.25M $CaCl_2$. The mixture was mixed with an equal volume of 2×HBS (Hanks Buffer Salt, available from GIBCO, Grand Island, N.Y.) to create a mixture containing 1 µg/mL p$\beta$-Gal. The opaque mixture was incubated at room temperature for 10 minutes and then applied to the cells. The suspended cells were incubated for 2 hours at 37° C. and under 5% $CO_2$. The cells were then washed with fresh medium and re-plated.

The replated cells were incubated for 48 hours in DMEM medium containing 10% FCS. During the incubation, the medium was replaced with fresh medium at 16 hours. After the 48 hour incubation, the cells for each incubation were collected by scrapping, washed with PBS, and resuspended in 100 µl of 0.2M Tris-HCL (pH 7.4). The cells were lysed with several freeze/thaw cycles, and centrifuged at an excess of 6,000×/g. 50 µl of supernate was removed from each lysate tube and mixed with 50 µl of a solution of 0.1 mM 4-methyl-umbelliferril-$\beta$-D-galactopiraniside (the substrate), 0.1M sodium phosphate (pH 7.4). Each mixture was incubated for 20 min. at 37° C. to allow any $\beta$-galactosidase present to act on the substrate. 50 µl of 0.4M glycine, pH 10.5, was added to terminate the $\beta$-galactosidase reaction. $\beta$-galactosidase activity was indicated by the presence of methylbelliferon, which can be measured by fluorescence spectroscopy ($\lambda_{ex}$=365 nm, $\lambda$=450 nm). The results were:

| Treatment | Relative Enzyme Activity ± SEM (n = 4) |
| --- | --- |
| Pluronic A | 320 ± 42 |
| Calcium Phosphate Precipitation | 17 ± 5 |

EXAMPLE 2—TRANSFECTION EFFICIENCIES—FIRST EMBODIMENT COMPLEX

In these experiments, transfection efficiencies with MDCK cells (derived from canine kidney) were examined. Again, p$\beta$-Gal was the indicator polynucleotide. The polycation component of the polynucleotide comprised a copolymer of N-ethyl-4-vinylpyridinium bromide and N-cetyl-4-vinylpyridinium bromide, the monomers incorporated in a molar ratio of 97:3, respectively (hereinafter "pEVP-co-pCVP-Br"). The block copolymer comprised a triblock copolymer of formula (XIV) wherein x+z was 18 and y was 23 (hereinafter "Pluronic B"). A Pluronic B transfecting solution of 1 µg/ml p$\beta$-Gal, 3 µg/ml pEVP-co-pCVP-Br, and 1% (w/v) Pluronic B was prepared in Example 1. The ratio of polycation basic groups to nucleotide phosphates was about 7. The weight ratio of Pluronic B to pβ-Gal was about $5 \times 10^3$.

MDCK cells were plated at $8-10^5$ cells per plate onto 90 mm plates and incubated overnight under serum-containing growth medium. The serum containing medium was then replaced with serum-free medium, and the cells were incubated at 37° C., under 5% $CO_2$ for 24 hours. For the cells to be treated with polynucleotide complex, the medium was then replaced with 5 ml Pluronic B transfecting solution. The cells were incubated, with gentle rocking, at 37° C., under 5% $CO_2$. In control experiments, cells were transfected with polynucleotide complex, the medium was then replaced with 5 ml Pluronic B transfecting solution. The cells were incubated, with gentle rocking, at 37° C., under 5% $CO_2$, for 2 hours. In control experiments, cells were transfected using the calcium phosphate procedure as described above (except that plated cells, not suspended cells, were transfected).

After treatment with Pluronic B transfecting solution or calcium phosphate, the cells were washed 5–6 times with fresh medium. They were then incubated in DMEM containing 10% FCS for 48 hours at 37° C., under 5% $CO_2$. After the first 16 hours of this incubation, the medium was replaced. After the incubation, the cells were washed with PBS, released from their plates by trypsinization, and again washed with PBS. β-Galactosidase was measured as described for Example 1. The results were as follows:

| Treatment | Relative β-galactosidase activity ± SEM (n = 4) |
|---|---|
| Pluronic B | 910 ± 45 |
| Calcium Phosphate Precipitation | 81 ± 17 |

EXAMPLE 3—TRANSFECTION EXPERIMENTS—FIRST EMBODIMENT COMPLEX

In these experiments, transfection efficiencies with Chinese hamster ovary (CHO) cells were examined. The polynucleotic component of the polynucleotic complex was pβ-Gal. The polycation component comprised pEVP-Br. The block copolymer comprised an octablock copolymer formula (XVII), wherein i was equal to 10 and j was equal to 12 (hereinafter "Pluronic C" available from BASF). A Pluronic C transfecting solution of 1 µg/ml pβ-Gal, 4 µg/ml pEVP-Br, and 1% (w/v) Pluronic C was prepared as in Example 1. The ratio of basic groups to nucleotide phosphates was 10. The weight ratio of Pluronic C to pβ-Gal was $10^3$. The transfection protocol was the same as that used in Example 2. The results were as follows:

| Treatment | Relative β-galactosidase activity ± SEM (n = 4) |
|---|---|
| Pluronic B | 910 ± 45 |
| Calcium Phosphate Precipitation | 81 ± 17 |

EXAMPLE 4—BACTERIAL TRANSFORMATION—SECOND EMBODIMENT COMPLEX

In these experiments, transformation efficiencies using the MC5 strain of Bacillus subtilis were examined. The polynucleotide component of the polynucleotide complex was plasmid pBC16, a plasmid encoding tetracycline resistance. A block copolymer according to formula (VI) was used. In particular, the block copolymer was a poly(oxyethylene)-oly((N-ethyl-4-vinylpyridinium bromide) of formula (XXI), wherein i was 44, and j was 20. A stock solution of second embodiment polynucleotide complex was prepared consistent with the transfection solutions described above. The ratio of copolymer basic groups to DNA phosphates in the solution was 0.2. Bacteria were suspended in Spizizen II, a transformation media (see, Spizizen, F.N.A.S., U.S.A. 44:1072 (1958)), and alloquots of cells were incubated in varying concentrations of either polynucleotide complex or free pBC16. The cells were incubated with complex or free DNA for one hour at 37° C. Following the incubation, the cells were plated onto agar media containing 10 mg/ml tetracyline. The results, measured by the number of tetracycline-resistant colonies produced under each of the experimental conditions, were as follows:

| DNA concentration | Transformation ($10^6$ clones/ng DNA) | |
|---|---|---|
| (ng/ml) | Polynucleotide Complex | Free Polynucleotide |
| 5 | 300 (±15) | 0 |
| 10 | 450 (±22) | 3 (±1) |
| 20 | 400 (±26) | 3 (±4) |
| 50 | 220 (±17) | 20 (±5) |

EXAMPLE 5—PROTECTION FROM NUCLEASE

For this example, a complex of plasmid pTZ19 and a diblock copolymer of formula (XXI) (poly(oxyethylene)-poly((N-ethyl-4-vinylpyridinium bromide), wherein i was 44 and j was 20) was formed. The solution of polynucleotide complex dissolved in PBS contained about 4 µg/ml of plasmid and 20 µg/ml of diblock copolymer. These amounts resulted in a ratio of base groups in the polycation block to DNA phosphate groups of 5. For control incubations, an equivalent amount of free plasmid was dissolved in buffer. PVUII nuclease was added to solution samples containing free DNA or polynucleotide complex, and the amount of undigested, circular plasmid DNA, after various digestion times, was determined by electrophoresis in a polyacrylamide gel. See Kabanov et. al., Biopolymers, 31:1437–1443 (1991). The results were as follows:

| | Circular DNA (% of initial) | |
|---|---|---|
| Time of Incubation | Complex | Free DNA |
| 0 | 100 | 100 |
| 5 | 100 | 20 |
| 10 | 100 | 8 |
| 30 | 100 | 4 |
| 60 | 100 | 1 |
| 180 | 100 | 0 |
| 600 | 100 | 0 |

EXAMPLE 6—OLIGONUCLEOTIDE STABILIZATION

For this example, a complex containing an oligonucleotide complementary to the transcription initiation site of the HIV-1 tat gene ("anti-tat", comprising GGCTCCATTTCTTGCTC) was prepared using the diblock copolymer of formula (XIX) (polyoxyethylene-poly(L- alanine-L-lysine), wherein i is 44 and j is 8). The oligonucleotide complex was prepared in PBS Buffer (pH 7.0) at a concentration of 0.75 $OD_{260}/\mu l$ oligonucleotide. The ratio of polycation imino and amino groups to polynucleotide phosphate groups was about 50. The mixture was incubated for one hour at room temperature to allow for the formation of the complex. Then, the complex was purified by gel filtration chromatography on Sephadex G-25 using 0.05M NaCl as the eluent. The resulting solution of complex exhibited a concentration of 0.11 $OD_{260}/\mu l$ of oligonucleotide. A comparable solution of uncomplex oligonucleotide was prepared. An alloquot of murine blood plasma (10 µl) was mixed with an equal volume of oligonucleotide complex solution or a solution of free oligonucleotide. Samples were incubated at 37° C. for various time periods. To stop the reaction of the oligonucleotides with enzymes in the plasma, the samples were diluted with water and extracted with a water-saturated mixture of phenol: chloroform (1:1). The aqueous phase of the extraction was isolated, and the oligonucleotide therein was precipitated with 3% lithium perchlorate. The precipitate was washed with acetone, and then dissolved in 100 µl of water. The presence of undergraded oligonucleotide was determined by high performance liquid chromatography using a $C_{18}$-Silasorb column (4×90 mm, Gilson, France) and a gradient of acetonitrile in 0.05M triethylammoniumacetate (pH 7.0) as the eluent. The results were as follows:

|  | Undergraded oligonucleotide (%) | |
| --- | --- | --- |
| Time of Incubation | Complex | Free Oligo |
| 0 | 100 | 100 |
| 3 hours | 88 | 28 |
| 6 hours | 70 | 17 |
| 24 hours | 36 | 0 |

EXAMPLE 7—OLIGONUCLEOTIDE STABILIZATION

This example examined the stability of the oligonucleotide described in Example 6, when complexed with a diblock copolymer of formula (XX) (polyoxyethylene-polypropyleneimine/butyleneimine, wherein i is 44 and j is 4–8) was examined. The same methodologies that were applied in Example 6 were applied for this example, except that the oligonucleotide concentration was about 0.13 $OD_{260}/\mu l$. The results were as follows:

|  | Undergraded oligonucleotide (%) | |
| --- | --- | --- |
| Time of Incubation | Complex | Free Oligo |
| 0 | 100 | 100 |
| 3 hours | 70 | 28 |
| 6 hours | 57 | 17 |
| 24 hours | 28 | 0 |

EXAMPLE 8—ANTISENSE CELL INCORPORATION EFFICIENCIES

This experiment examined the effectiveness of "anti-MDR", an antisense molecule comprising a 17-chain oligonucleotide of sequence CCTTCAAGATCCATCCC complementary to positions 422–438 of the mRNA encoding the MDR1 gene product, in reversing multi-drug resistance in SKVLB cells. SKVLB cells are multi-drug resistant cells derived from a ovarian cancer cell line. The MDR1 gene has been identified as responsible for the multi-drug resistance in SKVLB cells. Endicott and Ling, *Ann. Rev. Biochem.* 58:137 (1989). In particular, the efficiency of the anti-MDR oligonucleotide in the polynucleotide complex of the invention and when in the free state was compared. As controls, the free and complexed form of the anti-tat oligonucleotide described above were also used. The polynucleotide complexes were formed with the diblock copolymer of formula (XX) (polyoxyethylene-polypropyleneimine/butyleneimine, where i was 44 and j was 9–10). The complexes were prepared by the procedures described in Example 6. The oligonucleotide concentration in the complex or in the free state was 0.17 $OD_{260}/\mu l$. The copolymer was present in the concentration sufficient to define a ratio of polycation block imino and amino groups to oligonucleotide phosphate groups of 10.

The SKVLB cells were incubated for 3 days at 37° C. under 5% $CO_2$ in the presence of free or complexed oligonucleotide (at a concentration of 20 µM based on oligonucleotide content). Fresh media including free or complexed oligonucleotide was added every 12 hours.

The daunomycin cytotoxicity ($IC_{50}$) with respect to the cells treated as described above was measured using the method of Alley et. al., *Cancer Res.*, 48:589–601. The results were as follows:

| Treatment of Cells | Daunomycin $IC_{50}$ (ng/ml) (n = 4) |
| --- | --- |
| Control (untreated cells) | 8.0 |
| Anti-MDR Complex | 0.3 |
| Anti-tat Complex | 8.2 |
| Free Anti-MDR | 2.1 |
| Free Anti-tat | 7.9 |

EXAMPLE 9—ANTISENSE OLIGONUCLEOTIDE DESIGNED TO INHIBIT HERPES VIRUS

This experiment utilized a 12-chain oligonucleotide, which had been covalently modified at its 5' end with undecylphosphate substituent and at is 3' end with a acridine group, was used. This oligonucleotide modification has been described by Cho-Chung et. al., *Biochemistry Int.*, 25:767–773 (1991). The oligonucleotide sequence utilized, CGTTCCTCCTGU, was complementary to the splicing site at 983–994 of the Herpes Simplex virus 1 ("HSV-1"). As a control, an equivalently modified sequence (AGCAAAAGCAGG) complementary to the RNA produced by influenza virus was utilized. The oligonucleotides were applied to HSV-1 infected cells in either the complexed or the free state. When a complex was utilized, the complex was formed with the diblock copolymer of formula (XIX) (polyoxyethylene-poly(L-alanine-L-lysine), wherein i was equal to 44 and j was equal to 8). Oligonucleotide complexes were formed as described in Example 6.

African marmoset kidney cells ("Vero" cells) were infected with HSV-1 virus (strain L2, obtained from the Museum of Virus Strains, D.I. Ivanovskii, *Inst. of Virol.*, Russian Federation), as described by Vinogradov et al., *BBRC*, 203:959 (1994). The infected cells were washed with PBS. After washing, fresh RPMI-1640 media containing 10% of fetal calf serum and free or complex oligonucleotide was added to the cell. The cells were then incubated at 37° C. under 5% $CO_2$ for 24 hours. The HSV-1 infectivity of the of the cell media was then determined using the patch production method described by *Virology, A Practical Approach*, Mahy, Ed., IRL Press, Washington, D.C., 1985. The results, utilizing varying concentrations of oligonucleotide, were as follows:

| Treatment | HSV-1 Infectious Titre (CPE$_{50}$/ml) (n = 7) Oligo Conc. | | |
|---|---|---|---|
| | 0.2 µM | 1.0 µM | 5.0 µM |
| Control (untreated infected cells) | 1.0 (±0.5) × 10$^6$ | 1.0 (±0.5) × 10$^6$ | 1.0 (±0.5) × 10$^6$ |
| Anti-HSV complex | 1.4 (±0.2) × 10$^2$ | 0.5 (±0.3) × 10$^2$ | 0 |
| Anti-influenza complex | 1.0 (±0.6) × 10$^6$ | 0.7 (±0.1) × 10$^6$ | 0.8 (±0.2) × 10$^6$ |
| Free Anti-HSV | 0.9 (±0.4) × 10$^5$ | 2.3 (±0.7) × 10$^3$ | 1.6 (±0.4) × 10$^2$ |
| Free Anti-Influenza | 1.1 (±0.4) × 10$^6$ | 0.9 (±0.2) × 10$^6$ | 0.6 (±0.3) × 10$^6$ |

EXAMPLE 10—ANTISENSE OLIGONUCLEOTIDE DESIGNED TO INHIBIT HERPES VIRUS

Unless otherwise noted, this example utilized the same procedures as were utilized in Example 9. The cells utilized were BHK cells, a Chinese hamster kidney cell line. When the complexed form of the oligonucleotides was used, the complex was formed with the diblock copolymer of formula (XVII) (polyoxyethylene-poly-L-lysine, wherein i was 44 and j was 30), using the procedure described in Example 6. The concentration of the stock solution of complex was 0.09 OD$_{b\ 260}$/µl. The ratio of polycation block imino and amino groups to oligonucleotide phosphates was 10. The oligonucleotides, in complexed or free form, were applied to the cells at a concentration of 3.0 µM. The results were as follows:

| Treatment of cells | HSV-1 infectious titre (CPE$_{50}$/ml) n = 7 |
|---|---|
| Control (untreated infected cells) | 10(±3) × 10$^3$ |
| Anti-HSV complex | 8(±6) |
| Anit-influenza complex | 13(±4) × 10$^3$ |
| Free Anti-HSV | 50(±14) × 10$^2$ |
| Free Anti-influenza | 9(±2) × 10$^3$ |

EXAMPLE 11—IN VIVO INHIBITION OF HSV

Polynucleotide complexes between the block copolymer of formula (XVII) (polyoxyethylene-poly-L-lysine, wherein i was 44 and j was 30) and the Anti-HSV and Anti-Influenza oligonucleotides were formed using the methods outlined in Example 9. The concentration of the stock solutions of complexes was 0.90OD$_{260}$/µl. The ratio of polycation block imino and amino groups to oligonucleotide phosphates was 10.

Inbred white mice (body weight: 6 to 7 g) were infected with HSV-1 (strain C1 from *Belorussian Res. Inst. of Epidemiol. & Microbiol*, Minsk) by intraperitoneal injection of 30 µl of a virus suspension (titre: 10$^{-7}$ LD$_{50}$/ml). Either Anti-HSV complex, Anti-Influenza complex, free Anti-HSV or free Anti-Influenza were injected (10 µl) into the tail vein of a given mouse at each of 2, 12, 24, 48 or 72 hours post-infection. The results were as follows:

| | Survived animals/ Amount of Animals in a group | | | |
|---|---|---|---|---|
| Treatment of mice | Exp. 1 | Exp. 2 | Exp. 3 | % Survival |
| Control (infected mice) | 1/9 | 1/10 | 2/10 | 13.7 |
| Anti-HSV complex | 8/9 | 6/10 | 7/10 | 73.0 |
| Anti-influenza complex | 2/10 | 0/10 | 1/10 | 10.0 |
| Free Anti-HSV | 1/10 | 1/10 | 0/10 | 7.0 |
| Free Anti-influenza | 0/9 | 1/10 | 0.10 | 7.0 |

EXAMPLE 12—PLASMA LIFE OF POLYNUCLEOTIDE COMPLEX

A $^{32}$P-labelled 17-mer (GGCTCCATTTCTTGCTC) complementary to the transcription initiation site of the HIV-1 tat gene was utilized in this example. The oligonucleotide was modified at its 5'-end with cholesterol as described by Boutorin et al., *Bioconjugate Chemistry*, 2:350–356 (1990). A polynucleotide conjugate of the oligonucleotide was formed with the block copolymer of formula (XX) (polyoxyethylene-poly(propyleneimine/butyleneimine), wherein i was 44 and j was 9 to 10). The concentration of the stock solution (dissolved in PBS) of complex was 0.18 OD$_{260}$/µl. The ratio of polycation block imino and amino groups to oligonucleotide phosphates was 50.

Male C57/B1/6 mice (weight: 20–24 g; obtained from Russian Research Center of Molecular Diagnostics and Therapy, Moscow) received 50 µl intravenous injections of Anti-HIV conjugate or free Anti-HIV, at 0.18 OD$_{260}$/µl dissolved in PBS. At defined times after the injections, blood sample were taken from the tail vein and the animals were sacrificed. The amount of radioactive material in blood or tissue sample was determined by liquid scintillation counting (after appropriate solubilizations). The results were as follows:

| Time after injection (min) | Plasma levels (% of injected dose) | | Liver levels (% of injected dose) | |
|---|---|---|---|---|
| | Anti-HIV Conjugate | Free Anti-HIV | Prep. A | Prep. B |
| 0 | 100 | 100 | 0 | 0 |
| 5 | 95 | 58 | 3 | 7 |
| 10 | 91 | 40 | 5 | 19 |
| 15 | 84 | 33 | 7 | 26 |
| 20 | 79 | 27 | 9 | 30 |
| 30 | 75 | 20 | 10 | 35 |

EXAMPLE 13—CATIONIC BLOCK COPOLYMER SYNTHESIS 1,4-dibromobutane (5.4 g, 25 mmoles, from Aldrich Co., Milwaukee, Wis.) was added to a solution of N-(3-aminiopropyl)-1,3-propanediamine (6.55 g, 50 mmoles, from Aldrich Co.) dissolved in 100 ml of 1,4-dioxane. This reaction mixture was stirred at 20° C. for 16 h. The product of this reaction spontaneously precipitates from solution as the hydrobromide salt. This precipitated first intermediate was collected and twice dried by rota-evaporation from a solution of 10% triethylamine in methanol. This evaporation procedure was effective to remove substantial amounts of the bromide salt. The first intermediate was dissolved in 50 ml of 1,4-dioxane and reacted with 2.7 g (12.5 mmoles) of 1,4-dibromobutane. Again, the reaction proceeded for 16 h at 20° C., and the resulting second intermediate was recovered and dried as above. The second intermediate was neutralized with acetic acid to a pH of 7–8 and purified by gel filtration on Sephadex G-25, using an aqueous eluent. Three major polymine fractions were obtained, having apparent molecular weights of 1060, 700 and 500, respectively.

Poly(oxyethyleneglycol) (1.5 g, M.W. 1500, from Fluka) was dissolved in 8 ml of 1,4-dioxane and reacted with 0.17 g (1 mmole) of N,N'-carbonylimidazole (Aldrich Co.) at 20° C. for 3 h. The reaction mixture was divided into two parts. Each part was mixed with 4 ml of a 10% (w/v) solution of either the 1060 or 700 MW polyimine fraction, which solution further contained 0.01N NaOH. The mixture was stirred for 16 h at 20° C. From this mixture, block copolymers of formula (XX) and various MW ranges were isolated by gel filtration.

EXAMPLE 14—CATIONIC BLOCK COPOLYMER SYNTHESIS 0.5 g of a succinimidyl carbonate of methoxy-PEG (MW 5000, Shearwater Polymers, Inc., USA) was dissolved in 1,4-dioxane. This dioxane solution was added to an aqueous solution containing 0.2 g of the 1060 MW polyimine polymer described above, which aqueous solution further included 0.01N NaOH. This reaction mixture was stirred at 20° C. for 16 h. A polymer of formula (XXII) was isolated from the reaction by gel filtration.

EXAMPLE 15—CATIONIC BLOCK COPOLYMER SYNTHESIS 1.5 g of poly(oxyethyleneglylol) (MW 8000, Fluka) were dissolved in 8 ml of 1,4-dioxane. 0.34 g (2 mmole) of N,N'-carbonylimidazole (Aldrich Co.) were added to the solution and reacted for 3 h at 20° C. 8 ml of an aqueous solution containing 0.01N NaOH and 15% (w/v) of the 500 MW polyimine polymer described above in Example 13 was then added to the first reaction mixture. The resulting mixture was reacted for 16 h at 20° C. with stirring. A polymer of formula (XXIII) was isolated from the second reaction mixture by gel filtration.

EXAMPLE 16—CONJUGATE SYNTHESIS WITH OLIGONUCLEOTIDE

A 12-mer oligonucleotide, 5'-CGTTCCTCCTGU ("Oligo A") complimentary to the splicing site (positions 983–994 on the viral genome) of the early mRNA of type 380 Herpes SimplexVirus ("HSV-1"), was synthesized using a 380B-02 DNA-synthesizer (Applied Biosystems, CA). The synthesizer used phosporamidite chemistry and an 8 min. synthesis cycle. Cycle conditions and preparation of the crude product were done as recommended by Applied Biosystems. The crude Oligo A obtained from the synthesis was precipitated from a 1M LiCl solution (0.5 ml) with acetone (2 ml). The precipitate was dissolved in triethylammonium acetate buffer and purified by reverse-phase high performance liquid chromatography on a Silasorb C18 column (9×250 mm, Gilson, France) developed with an acetonitrile gradient in a 20 mM TEAA buffer (pH 8.5).

The 3'-terminal of the purified Oligo A was oxidized with periodate to create an aldehyde and conjugated by reductive alkylation with a hexamethylene-diamine linker, creating an amine derivative. See Che-Chung et al., *Biochem. Internat.*, 25:767 (1991); Vinogradov et al., *BBRC*, 203:959 (1994). "Pluronic A", a block copolymer of formula (XIV)(x=25, y+38, z=25) was similarly oxidized to create terminal aldehydes. The amine derivative (1 mg) was dissolved in 100 μl of 0.1M borate buffer (pH 9.0) and mixed with 2 mg of the Pluronic A derivative. 1.5 mg of sodium cyanoborohydride was added to the mixture to reduce the Schiff's bases formed between the amine and aldehyde groups. This reaction was allowed to proceed for 12 hours at 4° C. The polymeric product of this reaction was isolated by gel filtration chromatography on Sephadex LH-20, utilizing 90% aqueous isopropanol as the eluent. The conjugate so obtained is referred to hereinafter as "Oligo A Conjugate."

EXAMPLE 17—THE EFFECT OF OLIGO A CONJUGATE ON VIRUS PRODUCTION

Oligo A and Oligo A Conjugate were separately dissolved in RPMI 1640 medium (ICN Biomedicals Inc., Costa Mesa, Calif.) to a final concentration of 0.2 mM (based on oligonucleotide absorbance). These stock solutions were then filtered through 0.22 μm filters to remove any possible bacterial or fungal contamination.

Monolayers of Vero cells were incubated for 1 hour at 37° C. in serum-free RPMI 1640 together with various concentrations of Oligo A or Oligo A Conjugate. The monolayers, while still exposed to oligonucleotides, were then infected with 1 plaque forming unit per cultured cell of HSV-1, strain L2 (from the Museum of Virus Strains of the D.I. Ivanovskii Institute of Virology, Russian Academy of Sciences, Russian Federation). This infection method has been described by Vinogradov et al., *BBRC*, 203:959 (1994). After 8 hours of exposure to virus and oligonucleotides, the medium on the cells was replaced with fresh medium containing 10% FCS. Medium from the cells was collected at 22 and 39 hours after the infective incubation, and the virus titer in the collected medium was determined as described in *Virology, A Practical Approach*, Mahy, Ed., IRL Press, Oxford Univ. Press, Washington, DC, 1985. The results were as follows:

| Sample concentration (mM) | Oligonucleotide concentration (μM) | Infectious Titer of HSV-1 (PFU/ml) | |
| --- | --- | --- | --- |
| | | 22 hours past infection | 39 hours past infection |
| Control (cells without oligonucleotides | 0 | $5 \times 10^6$ | $1 \times 10^7$ |
| Oligo A | 10 | $3 \times 10^6$ | $5 \times 10^6$ |
| | 5 | $5 \times 10^6$ | $1 \times 10^7$ |
| | 2 | $5 \times 10^6$ | $1 \times 10^7$ |
| | 1 | $5 \times 10^6$ | $1 \times 10^7$ |
| Oligo A Conjugate | 10 | 0 | 0 |
| | 5 | 0 | $5 \times 10^2$ |
| | 2 | $1 \times 10^3$ | $7 \times 10^3$ |
| | 1 | $5 \times 10^4$ | $3 \times 10^6$ |

EXAMPLE 18—SYNTHESIS OF A PHOSPHONATE MONOMER 40 mmoles of butanediol-1,3 (Merck) dissolved in 50 ml of anhydrous pyridine (Aldrich) were reacted with 20 mmoles 4,4'-dimethoxytritylchloride (Sigma) for 1.5 hours at 20° C. The reaction was monitored using thin layer chromatography on the silicagel plates (Merck) developed with a chloroform:methanol (95:5). The Rf of the product was 0.6. The reaction mixture was added to 200 ml of an 8% aqueous solution of the sodium bicarbonate and the product extracted with chloroform. The chloroform extract was evaporated in vacuum and the resulting oily first intermediate was used in the next stage of the synthesis.

12 mmoles of first intermediate were dissolved in 30 ml of anhydrous 1,4-dioxane, containing 3.14 ml (18 mmloes) of diisopropylethylamine (Aldrich). 18 mmoles of salicylchlorophosphite (Sigma) dissolved in 10 ml of anhydrous 1,4-dioxane were added to the diisopropyethylamine solution in small portions under an inert, argon atmosphere. The reaction mixture was incubated during 1 hour at 20° C. The reaction was monitored by the thin layer chromatography as described above. The Rf of the product was 0.05. 10 mls of water were added to the reaction mixture. After 30 min., the solvent was evaporated. The product was dissolved in 100 ml of chloroform and the solution obtained was washed stepwise with (1) 100 ml of 8% aqueous solution of the sodium bicarbonate, (2) 100 ml of 0.2M triethyammoniumacelate solution (pH 7.2), and (3) 100 ml of water. The organic solvent was evaporated and the oily remainder, containing the phosphonate monomer was purified by chromatography on silicagel column, using stepwise gradient of (1) chloroform, (2) 3% methanol in chloroform and (3) 6% methanol in chloroform. The yield of the monomer was 4.1 g (=7.3 mmol, 63%). The product, having structure

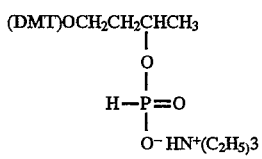

wherein DMT represents a dimethoxytrityl group, can be termed "Phosphonate Monomer A."

EXAMPLE 19—SYNTHESIS OF POLYCATION BDP

A 0.05M solution of the phosphonate Monomer A in anhydrous pyridine:acetonitrile mixture (1:1) was placed in the position 6 of the DNA-synthesator (model 380-B02, Applied Biosystems, CA). A 2% solution of adamantoilchloride (Sigma) in the mixture acetonitrile:pyridine (95:5) was used as a condensing agent. The synthesis was conducted using the program modified for an H-phosphonate cycle (sigma and Striepeke In: *Oligonucleotides and Analogues: A Practical Approach*, Eckstein Ed. IRL Press, Oxford, New York-Tokyo, p. 185, 1991) and the DMT-group was preserved after the synthesis was complete. Adenosine (4 µmoles) immobilized on a standard CPG-500 solid support was used as a first unit during the polymer synthesis (Vinogradov et al. *BBRC*, 203, 959 (1994). The synthesizer was programmed to add 15 Phosphonate Monomer A repeating units to the adenosine monomer. Following all synthesis steps, the H-phosphonate groups on the immobilized substrate were oxidized with the solution of 104 mg of hexamethylenediamine (Sigma) in 0.6 ml of a mixture of anhydrous pyridine:CCl$_4$ (5:1) applied for 15 min. at 20° C., then the carrier was washed with the pyridine:acetonitrile mixture (1:1). Deblocking and cap removal was achieved by ammonolysis (*Oligonucleotides and Analogues. A Practical Approach*, Eckstein Ed. IRL Press, Oxford, New York-Tokyo, 1991). The product was purified by HPLC using Silasorb C$_{16}$ column (9×250 mm. Gilson, France) in the acetonitrile gradient (0–80%). The peak, containing dimethoxytritylated-product was collected, the solvent was evaporated and the remainder was treated with 80% acetetic acid (20 min). The acetic acid was evaporated and the polycation was purified again by HPLC. The yield of the 15-mer (counted in terms of Phosphonate Monomer A) is 50% (2.2 µmoles). This created a polymer according to formula A. The polymer will be termed hereinafter "BDP."

EXAMPLE 20—SOLID PHASE SYNTHESIS OF THE DIBLOCK COPOLYMER POLYOXYETHYLENE-BDP

Dimethoxytrityl-polyethyleneoxide-H-phosphonate was synthesized as described in Example 18 using polyethyleneglycol (1500 M.W. from Fluka) instead of butanediol-1,3. The BDP polycation was synthesized as described in Example 19, except that, at the last stage of the chain growth, dimethoxytrityl-polyethyleneoxide-H-phosphonate was introduced as the last building block. The H-phosphonate groups of the block copolymer were oxidized as described in Example 19 using tetramethylenediamine (Sigma) instead of hexamethylenadiamine, resulting in the formation of phosphoamide bonds between the diamines and the backbone phosphates.

EXAMPLE 21—Solid PHASE SYNTHESIS OF THE OLIGONUCLEOTIDE-BDP DIBLOCK COPOLYMER A diblock copolymer comprising 12-mer oligonucleotide, 5'-GGTTCCTCCTGU (Oligo A, complementary to the splicing site of the early mRNA of type 1 Herpes Simplex Virus (HSV-1), Vinogradov et al. *BBRC*, 203, 959 (1994)) and the BDP polymer was synthesized in DNA synthesator. First the BDP polymer was synthesized as described in Example 19, except that it was not removed from the support. Then the oligonucleotide chain was synthesized step-wise onto BDP polycationic polymer linked to the solid state support using the standard phosphoroamidite chemistry as described by Vinogradov et al. *BBRC*, 203, 959 (1994). The H-phosphonate groups of the diblock copolymer were oxidized as described in Example 19 using tetamethylenediamine (Sigma) instead of hexamethylenediamine.

EXAMPLE 22—THE EFFECT OF THE OLIGONUCLEOTIDE-BDP DIBLOCK COPOLYMER ON THE VIRUS GROWTH

The experiment was performed exactly as described in Example 17 except that (1) the oligonucleotide-BDP copolymer of Example 21 was used and (2) a single concentration of oligonucleotide-BDP copolymer (conjugate) was used (4 µM).

| Sample | Virus titre after 39 hours |
|---|---|
| Control (without oligonucleotide) | $500 \times 10^4$ |
| Nonmodified Oligo A | $500 \times 10^4$ |
| Diblock | $5 \times 10^4$ |

What is claimed:

1. A polynucleotide composition comprising:
   (a) a polynucleotide or nucleic acid molecule which has been covalently modified; and
   (b) a copolymer of covalently bound polymer segments wherein said segments comprise
      (i) at least one poly-ether segment which is:
         (a) a homopolymer of the ethyleneoxy monomer —OCH$_2$CH$_2$— or
         (b) a copolymer or block copolymer of said ethyleneoxy monomer and the monomer —OCH(CH$_3$)CH$_2$—,
      each of said polyether segments having from about 5 to about 400 monomeric units, and
      (ii) at least one polycation segment which is a cationic homopolymer, copolymer, or block copolymer which is the reaction product of at least three amino-containing monomers, or quaternary salts thereof, said amino-containing monomers being selected from the group consisting of
- (a) same or different units of the formula —NH—$R^o$— in which $R^o$ is straight chain alkylene of 2 to 6 carbon atoms;
- (b) a cationic amino acid;
- (c) (—OPO(NH—$R^9$—$NH_2$)O—$R^8$—) in which $R^9$ is a straight chain aliphatic group of from 1 to 12 carbon atoms and $R^8$ is —$(CH_2)_n$—CH($R^{13}$)— where n is an integer from 0 to 5 and $R^{13}$ is hydrogen, cycloalkyl having 3–8 carbon atoms, or alkyl of 1–6 carbon atoms; and
- (d) 4-vinylpyridine.

2. The polynucleotide composition according to claim 1 wherein said copolymer has the formula:

A-R, A-R-A', or R-A-R', wherein each of A and A' is a homopolymer of the ethyleneoxy monomer —$OCH_2CH_2$—, or a copolymer or block copolymer of said ethyleneoxy monomer and the monomer —$OCH(CH_3)CH_2$—, and each of R and R' is a polycation segment as therein defined.

3. The polynucleotide composition according to claim 2 wherein R and R', at physiological pH, comprise at least six cationic groups.

4. The polynucleotide composition according to claim 2 wherein R and R', at physiological pH, contain a plurality of cationic groups separated by about 3 Å to about 12 Å.

5. A copolymer of covalently bound polymer segments wherein said segments comprise:
- (i) at least one polyether segment which is:
  - (a) a homopolymer of the ethyleneoxy monomer —$OCH_2CH_2$— or
  - (b) a copolymer or block copolymer of said ethyleneoxy monomer and the monomer —OCH($CH_3$)$CH_2$—, each of said polyether segments having from about 5 to about 400 monomeric units, and
- (ii) at least one polycationic segment which is a homopolymer, copolymer, or block copolymer comprising at least three amino-containing monomers, or quaternary salts thereof, which are same or different units of formula —NH—$R^o$— wherein $R^o$ is a straight chain aliphatic group of 2 to 6 carbon atoms, which may be substituted.

6. A block copolymer according to claim 5 having the formula:

A-R, A-R-A', or R-A-R', wherein each of A and A' is a homopolymer of the ethyleneoxy monomer —$OCH_2CH_2$— or a copolymer or block copolymer of said ethyleneoxy monomer and the monomer—OCH($CH_3CH_2$—, and each of R and R' is a polycationic segment as therein defined.

7. A polynucleotide composition according to claim 1 wherein each of said polyether segments has from about 5 to about 80 monomeric units and said polycationic segment is a homopolymer, copolymer, or block copolymer of from about 2 to about 180 of the same or different monomeric units of the formula —NH—$R^o$— in which $R^o$ is as therein defined.

8. A polynucleotide composition according to claim 1 wherein said polyether segment is a homopolymer of —$OCH_2CH_2$ and said polycationic segment is a homopolymer of —$NHCH_2CH_2CH_2$— or a copolymer of —$NHCH_2CH_2CH_2$— and —$NHCH_2CH_2CH_2CH_2$—.

9. A polynucleotide composition according to claim 8 wherein said polycationic segment is a homopolymer of —$NHCH_2CH_2CH_2$—.

10. A copolymer according to claim 5 wherein each of said polyether segments has from about 5 to about 80 monomeric units and said polycationic segment is a homopolymer, copolymer, or block copolymer of from about 2 to about 180 monomeric units.

11. A copolymer according to claim 5 wherein said polyether segment is a homopolymer of —$OCH_2CH_2$ and said polycationic segment is a homopolymer of —$NHCH_2CH_2CH_2$— or a copolymer of —$NHCH_2CH_2CH_2$— and —$NHCH_2CH_2CH_2CH_2$—.

12. A copolymer according to claim 11 wherein said polycationic segment is a homopolymer of —$NHCH_2CH_2CH_2$—.

* * * * *

UNITED STATES PATENT AND TRADEMARK OFFICE
CERTIFICATE OF CORRECTION

PATENT NO. : 5,656,611
DATED : August 12, 1997
INVENTOR(S) : Kabanov, et al.

It is certified that error appears in the above-identified patent and that said Letters Patent is hereby corrected as shown below:

On the title page,

In the Inventors, item [75], should read "Alexander Victorovich Kabanov, Omaha, Nebraska, Valery Yulievich Alakhov, Baie d'Urfe, Quebec, Canada; Sergey V. Vinogradov, Moscow, Russian Federation In the Assignee, item [73], should read "Supratek Pharma Inc., Montreal, Quebec, Canada Signed and Sealed this Sixth Day of July, 1999

Attest:

Q. TODD DICKINSON

*Attesting Officer*     Acting Commissioner of Patents and Trademarks